(12) United States Patent
Tian et al.

(10) Patent No.: US 12,209,943 B2
(45) Date of Patent: Jan. 28, 2025

(54) ISOLATED CELL MEMBRANE POTENTIAL DETECTION SYSTEM AND METHOD BASED ON MULTI-SPECTRAL MULTI-PARAMETER PHOTOSTIMULATION

(71) Applicant: SHANDONG UNIVERSITY, Shandong (CN)

(72) Inventors: Lan Tian, Shandong (CN); Yanqing Wang, Shandong (CN); Jingjing Xu, Shandong (CN); Ming Zeng, Shandong (CN); Wei Liu, Shandong (CN); Xu Tian, Shandong (CN); Xiaoshan Lu, Shandong (CN)

(73) Assignee: SHANDONG UNIVERSITY, Shandong (CN)

( * ) Notice: Subject to any disclaimer, the term of this patent is extended or adjusted under 35 U.S.C. 154(b) by 0 days.

(21) Appl. No.: 18/567,880

(22) PCT Filed: Sep. 16, 2022

(86) PCT No.: PCT/CN2022/119390
§ 371 (c)(1),
(2) Date: Dec. 7, 2023

(87) PCT Pub. No.: WO2023/041053
PCT Pub. Date: Mar. 23, 2023

(65) Prior Publication Data
US 2024/0264067 A1    Aug. 8, 2024

(30) Foreign Application Priority Data
Sep. 18, 2021   (CN) .......................... 202111111952.7

(51) Int. Cl.
G01N 15/1031   (2024.01)
G01N 15/10     (2006.01)

(52) U.S. Cl.
CPC . G01N 15/1031 (2013.01); *G01N 2015/1006* (2013.01)

(58) Field of Classification Search
None
See application file for complete search history.

(56) References Cited

FOREIGN PATENT DOCUMENTS

| CN | 101285825 A | 10/2008 |
|----|-------------|---------|
| CN | 107462745 A | 12/2017 |

(Continued)

OTHER PUBLICATIONS

Wells et al. "Pulsed laser versus electrical energy for peripheral nerve stimulation" (2007), J Neurosci Methods, vol. 163: 326-337. (Year: 2007).*

(Continued)

*Primary Examiner* — Teresa E Knight
(74) *Attorney, Agent, or Firm* — The PL Law Group, PLLC (57) ABSTRACT

An isolated cell membrane potential detection system can measure a cell membrane current change when light having different parameters such as wavelength, energy density, pulse width, and repetition rate stimulates a cell to be detected, to detect whether the biological electrical activity of the cell can be regulated by light, and to detect the specificity of the light regulation parameters of the cell. In the light regulation cell membrane potential detection system, a method of progressively adjusting and detecting with multiple optical parameters from small to large is used to measure a cell membrane current change in different periods under a certain photostimulation parameter for each group of cells, so as to quickly and efficiently detect which type of optical signal can regulate the characteristics of the cell such as the generation of a membrane current, photostimulation parameter specificity, and an energy threshold.

5 Claims, 4 Drawing Sheets

(56) References Cited

FOREIGN PATENT DOCUMENTS

CN  111103272 A  5/2020
CN  113702268 A  11/2021
WO  WO 2015/016419 A1  2/2015

OTHER PUBLICATIONS

International Search Report for PCT/CN2022/119390 mailed on Nov. 28, 2022.

* cited by examiner

ISOLATED CELL MEMBRANE POTENTIAL DETECTION SYSTEM AND METHOD BASED ON MULTI-SPECTRAL MULTI-PARAMETER PHOTOSTIMULATION

PRIORITY

This application claims benefit under 35 U.S.C. 119, 120, 121, or 365(c), and is a National Stage entry from International Application No. PCT/CN2022/119390 filed on Sep. 16, 2022, which claims priority to the benefit of Chinese Patent Application No. 202111111952.7 filed in the Chinese Intellectual Property Office on Sep. 18, 2021, the entire contents of which are incorporated herein by reference.

BACKGROUND

1. Technical Field

The present disclosure belongs to the fields of neuroscience, optics, life science, electronic technology and the like, and specifically relates to a system and method for detecting a cell membrane potential under multi-spectral multi-parameter photostimulation.

2. Background of the Invention

Excitation or inhibition of excitable cells in animals can be regulated by physical stimulation signals under different conditions, for example: a nerve cell of an animal may be excited by photostimulation. When an ion channel on the nerve cell responds to a physical stimulation signal, the intracellular and extracellular ion concentrations may be changed to generate a membrane current, and then cause a change in the cell membrane potential, namely a nerve action potential, so that the cell is excited. The phenomenon that photostimulation induces a change in the intracellular icon concentration and a change in the intracellular and extracellular potentials to generate a membrane current belongs to the cell photosensitive effect.

There are several mechanisms by which light induces a membrane current in a cell and thus alters the cell membrane potential, such as: a photothermal effect, a photomechanical effect, a photochemical effect, or the like. The presence of a photosensitive ion channel in cell membrane is one of the causes of the membrane current. The photosensitive channel is a specific or selective ion channel with a transmembrane structure and controlled by light pulses, which channel can quickly form a membrane current and enable a cell to generate an electrophysiological reaction. It has been found that there are a variety of photosensitive ion channel proteins in nature.

There are many urgent issues to be studied, for example, in animals, in addition to visual cells, which cells have photosensitive channel proteins or other factors that enable the cells to be activated by light to produce changes in the membrane potential, how to measure and screen out these cells, in which waveband, energy density, pulse width, repetition rate can the membrane current be induced, and so on.

In the research of life science, a common research paradigm is to firstly discover a protein, then separate substances therein by means of a spectrophotometer, a protein gel electrophoresis, or by other methods, study components of the protein by means of sequencing or the like, and detect functions of the protein by various means, such as: using calcium ion imaging, a patch clamp or other means to verify whether it is possible for the protein to enable light-induced changes in the cell membrane potential. This series of detection methods start from studying substances such as a channel protein, until finally verifying the light regulation characteristics of the channel protein, which is a very complicated process. There is still a need for a method that can detect a light-controlled cell membrane potential response efficiently and systematically directly using photostimulation.

SUMMARY

The present disclosure provides a cell membrane potential detection system based on multi-spectral multi-parameter photostimulation, as well as a corresponding detection method. When an excitable cell is stimulated by light, a membrane current can be generated through a photosensitive effect of the exciting light, so that the intracellular and extracellular membrane potentials may change. Based on this phenomenon, the present disclosure can, by detecting such a change in the membrane potential (current), detect whether activity of the cell to be detected can be regulated by light, as well as other corresponding characteristics, such as the photostimulation parameter specificity, the energy threshold value of the light regulation action on the cell to be detected, and the like.

The technical solutions adopted by the present disclosure are described below:

In a first aspect, the present disclosure provides a cell membrane potential detection system based on multi-spectral multi-parameter photostimulation, including an operation desk on which a culture dish is placed, wherein the culture dish contains a nerve cell bath (such as artificial cerebrospinal fluid) which is similar to nerve cell interstitial fluid, capable of maintaining nerve cell activity and contains various ions, a nerve cell to be detected is placed in the bath, a microscope is disposed above the culture dish, and the culture dish is provided with a measuring electrode on one side and a photostimulation device on the other side: the measuring electrode is connected to a signal acquisition amplifier which is further connected to a measurement result recorder, and high-resistance sealing (for example, $G\Omega$) is formed between the measuring electrode and a nerve cell membrane.

As a further technical solution, the photostimulation device includes a multi-parameter programmable photostimulator connected to an optical fiber coupler that is connectable to an optical fiber for light guiding, the optical fiber is fixed through an optical fiber fixer, so that an output port of the optical fiber is fixed to a proper position where the nerve cell to be detected is irradiated.

As a further technical solution, the measuring electrode is a glass tube microelectrode including a glass tube and a measuring electrode, wherein the glass tube has a conical shape with an open tip having a diameter (for example, 1 to 2 μm) that can be drawn to be smaller than a size of a nerve cell body; and the measuring electrode is inserted into the glass tube from a tail part of the glass tube, while the glass tube is filled with an electrode internal solution which has substantially the same components as a nerve cell internal solution and is capable of maintaining activity of the cell.

As a further technical solution, the system further includes a reference electrode immersed in the nerve cell bath and connected to a signal ground terminal of the signal acquisition amplifier.

As a further technical solution, the photostimulation device includes a program adjustable optical parameter control module, a plurality of single-wavelength laser generation modules, and an optical fiber coupler, wherein the program adjustable optical parameter control module is configurable by a user to generate stimulating light with different parameters at regular intervals, control a stimulating light generation module of a corresponding wavelength to generate stimulating light with a corresponding parameter, and output the stimulating light through the optical fiber coupler.

As a further technical solution, optical parameters of the program adjustable optical parameter control module include: a duration, a light wavelength, a power density (or a light pulse intensity), a pulse width, and a pulse repetition rate.

In a second aspect, the present disclosure further provides an isolated cell membrane potential detection method based on multi-spectral multi-parameter photostimulation, including taking a nerve cell membrane potential (current) change as a representation phenomenon indicating that the nerve cell is capable of being regulated by light, and using a multi-parameter progressive (from small to large) regulation method for scanning measurement of optical parameters.

As a further technical solution, the nerve cell to be detected is a single isolated nerve cell, which is a nerve cell that is isolatedly cultured or surgically dissected.

As a further technical solution, the isolated cell membrane potential detection method based on multi-spectral multi-parameter photostimulation includes:
(1) treatment of the nerve cell: after the nerve cell is cultured isolatedly or separated acutely, using a glass tube microelectrode to measure the nerve cell membrane current change in an attached manner under different photostimulation conditions;
(2) photostimulation output mode: regulating photostimulation parameters by a multi-parameter program adjustable photostimulation device through a multi-parameter progressive scanning method; and
(3) measurement of specificity: performing membrane potential (current) measurement through progressive regulation of other optical parameters with different wavelengths of stimulating light, respectively, to detect wavelength specificity of the nerve cell regulated by light.

The present disclosure has the following beneficial effects:
1. When an excitable nerve cell is stimulated by light, a membrane current can be generated by exciting nerve cell activity, so that the membrane potentials inside and outside the nerve cell may change. Based on this phenomenon, the present disclosure can, by detecting such a change in the membrane potential or current, detect whether the nerve cell to be detected can be regulated by light, as well as other corresponding characteristics, such as the photostimulation parameter specificity, the energy threshold value during light regulation of the nerve cell to be detected and the like.
2. The present disclosure adopts a multi-parameter progressive regulation mode for measurement. For example: the light energy density is gradually regulated from small to large within a certain light pulse parameter range, such as gradually increased from 0 to 12 $mJ/mm^2$. In this manner, a strong optical signal is prevented from damaging or destroying the nerve cell activity, while enabling detection of whether the cell can be regulated by light, as well as a light energy threshold that can induce a membrane current or voltage.
3. The measuring system of the present disclosure can verify the light regulation wavelength specificity (also called selectivity of light wavelength) of the nerve cell by changing the wavelength of stimulating light and repeatedly measuring other optical parameters. The light regulation specificity of the nerve cell is embodied in the selectivity of light wavelength of the nerve cell. Therefore, the photostimulation device designed in the present disclosure can switch light wavelengths to measure the light regulation specificity of the nerve cell in the case of similar or progressively adjusted other optical parameters.

DETAIL DESCRIPTION

The present disclosure will be further illustrated below with reference to the specific examples. It should be understood that these examples are for illustrative purposes only and are not intended to limit the scope of the present disclosure. Experimental procedures without specific conditions noted in the following examples generally follow conventional conditions or conditions recommended by the manufacturer.

Unless defined otherwise, all technical and scientific terms used in the present disclosure have the same meaning as commonly understood by those skilled in the art. In addition, any method and material similar or equivalent to those described herein can be used in the methods of the present disclosure. The preferred methods and materials described in the present disclosure are for exemplary purposes only.

The present disclosure uses multi-spectral multi-parameter photostimulation to stimulate a nerve cell to be detected, judges whether the nerve cell to be detected can be regulated by light to active by measuring a membrane potential (current) of the nerve cell to be detected, and accurately detects the specificity and activation threshold of the light regulation parameters of the nerve cell. Specifically, the light regulation characteristics are measured by combining the photostimulation with the nerve cell membrane current. Whether the nerve cell membrane current is dramatically changed is taken as a basis for determining whether a certain optical parameter can induce a membrane current, and whether the nerve cell can be regulated by light.

Figure 1:
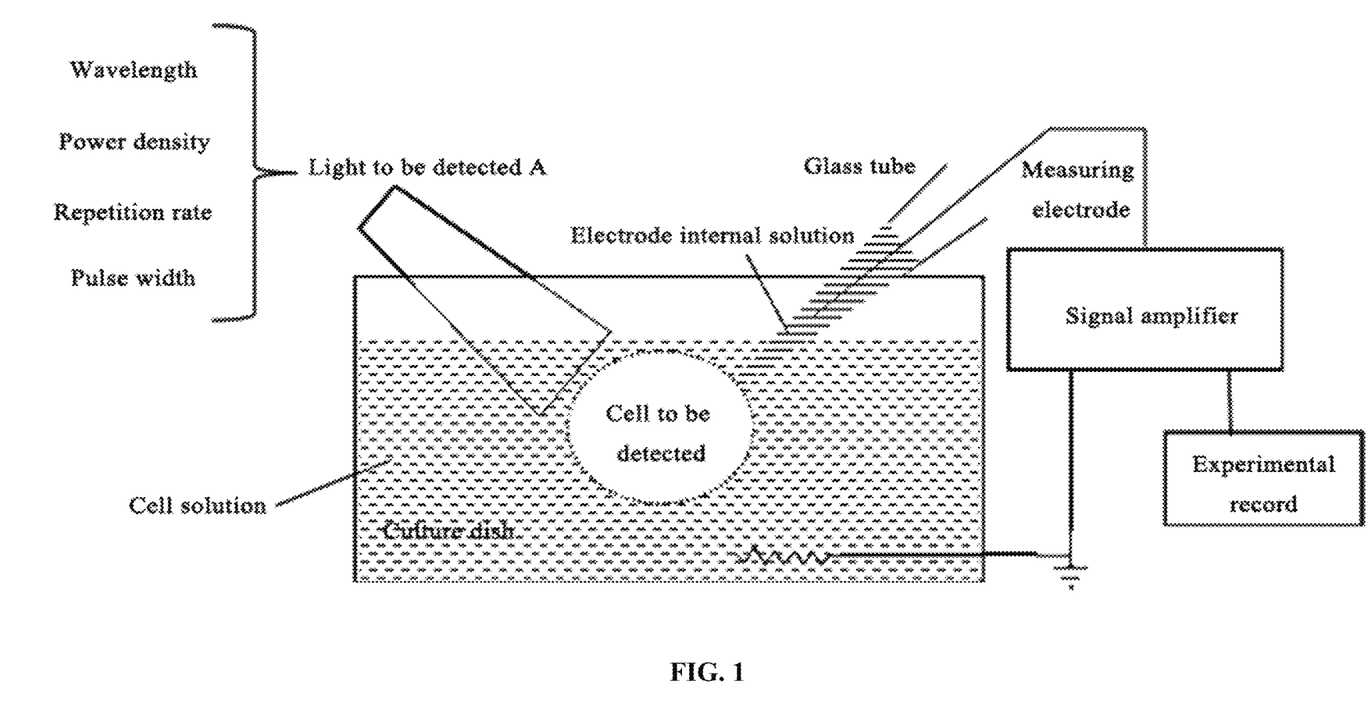
FIG. 1 is a schematic diagram of the present disclosure.

FIG. 1 is a schematic diagram of the present disclosure: in which the light to be detected A is an optical signal to be detected sent from a photostimulation device with multiple adjustable parameters (wavelength, power density, repetition rate and pulse width). The microelectrode in a glass tube is configured to measure a nerve cell membrane current. Changes in the nerve cell membrane current are collected by acquiring tiny current signals through a bioelectrical signal amplifier, and an experimental data recording system is configured to record and analyze the acquired signals.

The detection system provided by the present disclosure measures the intracellular membrane current and the membrane current of the nerve cell under photostimulation through a multi-wavelength photostimulation device with multiple adjustable parameters (energy density, pulse width, repetition rate and the like). If an optical signal of a certain parameter is detected to induce a change in the membrane current of the nerve cell to be detected or generate the membrane current, it indicates that activity of the nerve cell to be detected can be interfered and regulated by the optical signal of that parameter. In measurement of the membrane potential (current), only a certain type of stimulating light A with a single specific parameter is used within one measuring period, so that mutual interference of optical signals with different wavelengths is avoided. Throughout the measurement process, parameters of the stimulating light A are gradually adjusted based on a progressive policy, so that a light regulation response parameter threshold and a regulation range of the nerve cell to be detected are measured.

Figure 2:
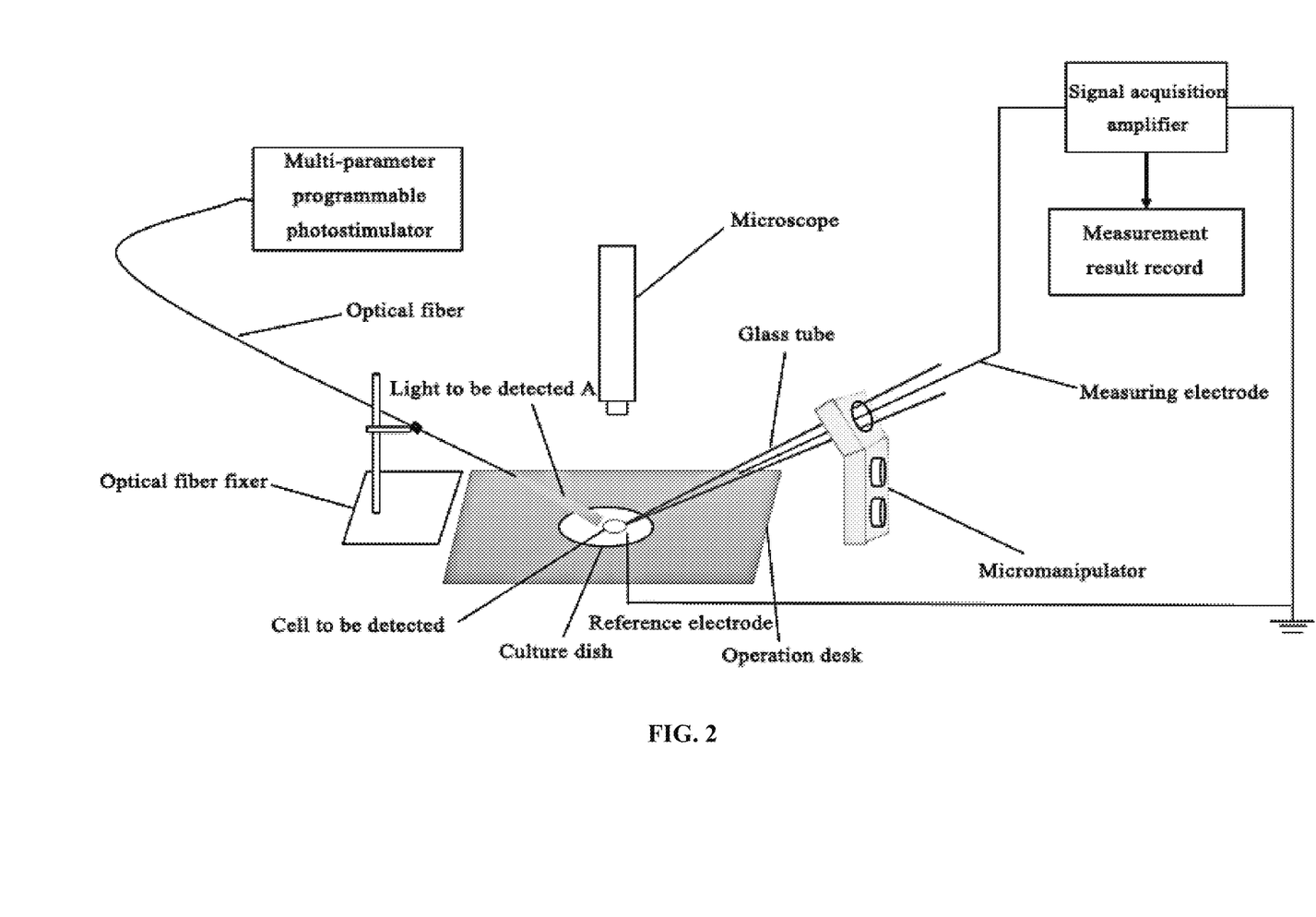
FIG. 2 is a schematic structural diagram of a detection system according to the present disclosure.

In FIG. 2, the detection system is composed of a multi-parameter programmable photostimulator, an optical fiber fixer, a microscope, a glass tube, a measuring electrode, a glass tube microelectrode operator, a nerve cell membrane current (potential) signal acquisition amplifier, a measurement result recording device, an operation desk and the like. A culture dish is placed on the operation desk and contains a nerve cell bath and a nerve cell to be detected. A microscope is disposed above the culture dish, and the culture dish is provided with a measuring electrode on one side and a multi-parameter programmable photostimulator on the other side. The measuring electrode is connected to the nerve cell membrane current (potential) signal acquisition amplifier which is further connected to a measurement result recording device, and high-resistance sealing (for example, GΩ) is formed between the measuring electrode and the nerve cell membrane. The multi-parameter programmable photostimulator is connected to an optical fiber coupler, and the optical fiber is fixed through an optical fiber fixer. A light source emitted from the multi-parameter programmable photostimulator, after being coupled and output through the optical fiber, is fixed by the optical fiber fixer to a position where the nerve cell to be detected can be irradiated.

The measuring electrode is a glass tube microelectrode including a glass tube and a measuring electrode. The glass tube has a conical shape with an open tip having a diameter (for example, 1 to 2 μm) smaller than a size of a single nerve cell body to be detected. The measuring electrode is inserted into the glass tube from a tail part of the glass tube, while the glass tube is filled with an electrode internal solution.

As a further technical solution, the system further includes a reference electrode immersed in the nerve cell bath and connected to a signal ground terminal of the signal acquisition amplifier.

Figure 3:
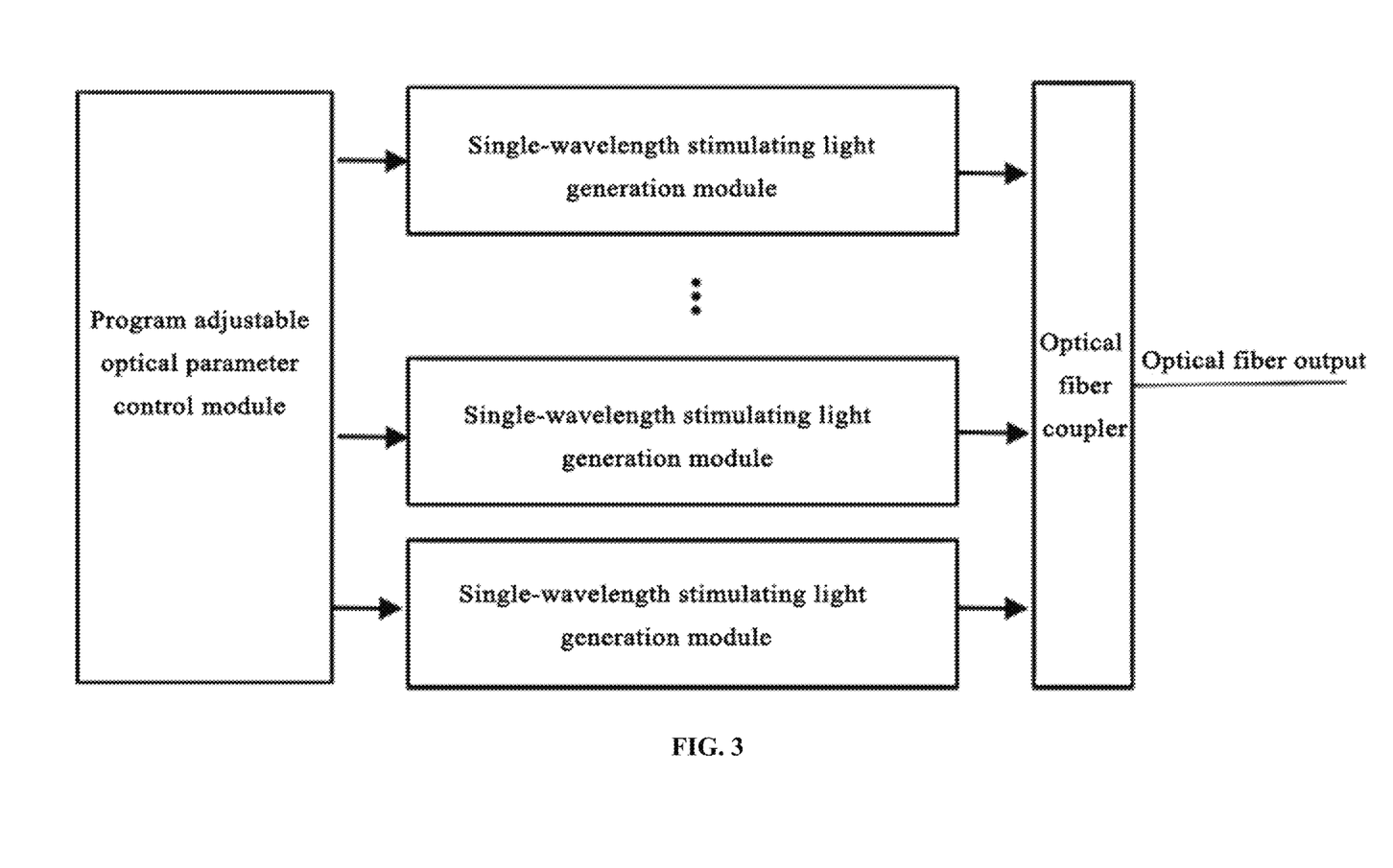
FIG. 3 is a multi-parameter adjustable photostimulation device for use in the present disclosure.

FIG. 3 is a multi-parameter adjustable photostimulation device for use in the present disclosure, which has three parts: a program adjustable optical parameter control module, a plurality of single-wavelength stimulating light generation modules, and an optical fiber coupler. The program adjustable optical parameter control module is configurable by a user to generate stimulating light with different parameters at regular intervals, control a stimulating light generation module of a corresponding wavelength to generate stimulating light with a corresponding parameter, and output the stimulating light through the optical fiber coupler.

According to the nerve cell membrane potential detection method based on multi-spectral multi-parameter photostimulation provided by the present disclosure, a nerve cell membrane potential (current) change is taken as representation of light regulated nerve cell activity, and a multi-parameter progressive regulation mode is used for scanning measurement of optical parameters. The parameters of the stimulating light include: a light wavelength, a pulse width, a repetition rate, a power density and other parameters. The nerve cell to be detected is a single isolated nerve cell, which may be a nerve cell that is isolately cultured or surgically dissected. The method includes the following specific steps:

selecting a nerve cell to be detected which has been cultured isolatedly for a proper time (such as 24 to 48 hours), or which is surgically dissected and acutely isolated: preparing an electrode internal solution, an extracellular fluid and other solutions required by measurement of a nerve cell membrane current, and manufacturing a glass microtube electrode and filling the glass microtube electrode with the electrode internal solution; and placing a culture dish containing the nerve cell to be detected on an observation platform with an inverted microscope, and forming high-resistance sealing (for example, GΩ) between the glass microtube electrode and the nerve cell membrane by an electrode operation desk.

The light source from the multi-parameter photostimulation system used in the present disclosure, after being coupled and output through the optical fiber, is fixed by the optical fiber fixer to a position where the nerve cell to be detected can be irradiated. Variation ranges of the stimulating light adjustable parameters are input, and parameters such as the energy density, the pulse width, the frequency and the like are adjusted within a certain period of time in a progressive mode from small to large, and a series of photostimulation of different optical parameters at the same wavelength is completed within a short time. Then, a tiny membrane current (such as pA level) signal at an electrode terminal is collected through a membrane current signal amplifier, and whether a nerve cell membrane current is induced under different parameters of photostimulation is recorded on an experiment recording system connected to the rear end. Then, different wavelengths of stimulating light are switched, and by scanning changes in the nerve cell membrane potential (current) in a progressive mode with the above optical parameters, whether the different wavebands of stimulating light induce the membrane current of the nerve cell to be detected and whether the light regulation of the nerve cell to be detected has wavelength specificity are detected. In FIG. 3, a schematic structural diagram of a photostimulation device used in the present disclosure is shown.

Different from other methods, the detection system used in the method of the present disclosure, in cooperation with the multi-wavelength multi-parameter adjustable photostimulation device mentioned in the present disclosure, scans the nerve cell membrane potential (current) in a progressive mode with optical parameters, so as to quickly detect whether a certain waveband of stimulating light with a certain parameter can induce a specificity effect of the membrane current of the nerve cell to be detected, and find an optical parameter threshold that excites the membrane current in a progressive scanning mode.

In the method, a policy of scanning and detecting with the optical parameters in a progressive mode from small to large within a certain range includes: using a stimulating light with a wavelength A, and progressively changing an optical power density at certain intervals, to measure a nerve cell membrane current response. Under the condition that other parameters remain unchanged, each stimulation period lasts for E seconds, and the photostimulation power density is changed by a value b each time. Assuming that the power density detection range is W, then the number of times n that the optical power density parameter needs to be changed is W/b, and the measurement time of this group is t=E·W/b, which means that the total measurement time within the specified power density variation range is n·E seconds. The progressive regulation and measurement of other optical parameters (such as the repetition rate, the pulse width and the like) are similar. For example: in a practical measurement, a pulsed laser with a wavelength of 450 nm is used, which has a pulse width of 200 us, a repetition rate of 11 Hz, and an average power density range of 0 to 12 $mJ/mm^2$, the power density is changed by 0.5 $mJ/mm^2$ each time, and the photostimulation lasts for Is each time. In this case, the single-wavelength multi-parameter scanning measurement time for the nerve cell is: 1×12/0.5=1×24=24 seconds.

EXAMPLES

In a specific embodiment, the present disclosure is implemented with a mouse auditory nerve cell as the cell to be detected, and the method includes the following steps:

1. Cell Culture and Specimen Preparation

A C57/BL newborn mouse is selected, from which a spiral ganglion cell in a cochlea dissected and taken out, digested and separated, and then placed in a culture dish with a cell slide for isolated culture with a temperature controlled at 37° C. and a gas environment of 95% air and 5% $CO_2$ for 24 hours before use. Before a test experiment, solutions required in the test process, such as a cell bath, an electrode internal solution and the like, are prepared. In measurement, the cell slide is placed in a culture dish containing the cell bath (artificial cerebrospinal fluid), and then placed on a microscope stage.

2. Parameter Setting of Photostimulation Device

The multi-parameter adjustable photostimulation device is configured according to the optical parameters for detection, so that stimulating light can be output according to the optical parameters in a progressive adjustment mode within a certain time period. For example: the laser wavelength is selected to be 450 nm, 515 nm, 808 nm, 980 nm, 1065 nm or other wavebands, the repetition rate is 1 Hz, a typical pulse width of the reference electric pulse stimulation is 200 μs, and the power density is 0 to 30 $mJ/mm^2$, progressively increased by a step of 0.5 mJ.

3. Manufacturing and Installation of Glass Tube Microelectrode

The glass tube microelectrode includes a conical glass tube and a measuring electrode. The specific manufacturing process includes: drawing a glass tube so that the glass tube has an open tip with a diameter of about 1 to 2 μm, inserting one end of the measuring electrode into the glass tube from a tail part, connecting the other end of the measuring electrode to a signal acquisition amplifier, filling the glass tube microelectrode with an electrode internal solution, and installing and screwing the microelectrode onto a micromanipulator, where the glass tube microelectrode filled with the electrode internal solution has an impedance of 5 to 10MΩ: connecting a reference electrode immersed in a cell bath to a signal ground terminal of the signal acquisition amplifier; and connecting the electrode internal solution in the microelectrode to a signal end of acquisition amplifier through the measuring electrode.

The reference electrode and the measuring electrode here are both made of Ag/AgCl.

4. Phase Boundary Potential Compensation and Electrode Resistance Measurement:

This step includes: applying a square wave voltage pulse of a small amplitude (5 mV) to the electrode, where only small capacitor current sharp waves superposed on a zero current baseline are observed: lightly applying a positive pressure to the interior of the microelectrode through a plastic pipe in communication with the microelectrode holder, controlling the microelectrode to enter the bath by a micromanipulator, where the current baseline immediately drifts away from zero, but gradually drifts back due to a negative feedback regulation effect, and response current square waves are superposed on the baseline; and adjusting phase boundary potential compensation so that the output current is zero, and measuring a resistance of the microelectrode according to an amplitude value of the current response caused by the pulse voltage square waves.

5. Cell Sealing

This step includes: selecting a neuron with a smooth surface, good transmittance and good state for experiments, adjusting the micromanipulator to enable the tip of the microelectrode to approach and press against a surface of the cell, releasing a positive pressure in the glass tube microelectrode, and then applying a negative pressure so that a sealing resistance reaches an order of GΩ, where the square wave current retracts to the baseline.

6. Fast Capacitance Compensation:

This step includes: increasing a current amplification factor, and adjusting equipment parameters to perform fast capacitive current compensation, so that the fast capacitive current component in the output current signal disappears.

7. Measurement of Cell Membrane Current Under Photostimulation

This step includes: before formally starting the cell membrane current measurement, fixing an output optical fiber on a photostimulation device through an optical fiber fixer, finely adjusting a position of the output optical fiber to enable the output light to irradiate a cell to be detected, then starting the photostimulation device to output stimulating light according to a set order, and controlling a potential inside the cell through a feedback function of the signal amplifier in a microelectrode voltage clamp mode, while starting measurement of the cell membrane current; and in the measurement process, replacing the cell sample to be detected in time according to the cell activity, and performing measurement of the cell membrane current at different time periods.

8. Data Analysis

Figure 4:
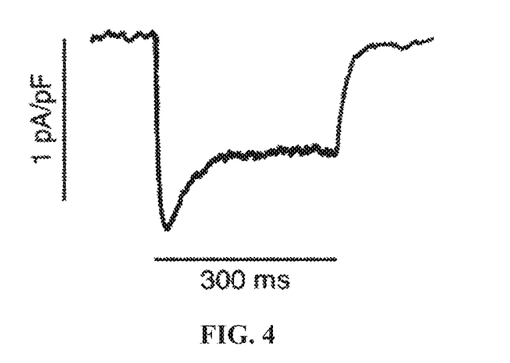
FIG. 4 is a graph showing a typical result of nerve cell membrane current measurement.

This step includes: checking and analyzing the measured membrane current data, and comparing the time periods to analyze under stimulation of which optical parameters, the membrane current has a notable change: finding out a corresponding photostimulation threshold and a dynamic response characteristic according to a time sequence relation of changes in the stimulating light parameters; and repeating and replacing the stimulating light wavelength for multiple times, to detect and analyze whether the light-regulated cellular activity has specificity. Under the light pulse stimulation with a wavelength of 450 nm, the experiment obtains the above change result of the cell membrane current, as shown in FIG. 4.

The detection method discussed above may be used for detecting unknown photosensitive effect of natural cells, or for verifying measurement of the cell membrane potential of transgenic cells under the stimulation of light with the wavelength corresponding to the specific photosensitive protein.

The descriptions above are merely preferred embodiments of the present disclosure, which are not used to limit the present disclosure. For those skilled in the art, the present disclosure may have various changes and variations. Any modification, equivalent replacement, improvement or the like made within the spirit and principle of the present disclosure shall be included in the protection scope of the present disclosure.

What is claimed is:

1. An isolated cell membrane potential detection method based on multi-spectral multi-parameter photostimulation, the method comprising:
   providing an isolated cell membrane potential detection system comprising:
   an operation desk;
   a culture dish placed on the operation desk, the culture dish containing a cell to be detected and a cell bath, wherein the cell bath is functionally similar to cell interstitial fluid, and is capable of maintaining cell activity;
   a microscope disposed above the culture dish;
   a measuring electrode on one side of the culture dish;
   a photostimulation device on the other side of the culture dish;
   a signal acquisition amplifier connected to the measuring electrode; and
   a measurement result recorder connected to the signal acquisition amplifier, wherein the photostimulation device includes:
   a multi-parameter programmable photostimulator;
   an optical fiber connected to the multi-parameter programmable photostimulator;
   an optical fiber coupler for inputting light generated by the multi-parameter programmable photostimulator into the optical fiber;
   a fixer for fixing the optical fiber so that an output port of the optical fiber is fixed to a position where the cell to be detected is irradiated;
   a program adjustable optical parameter control module;
   and a plurality of single-waveband waveband stimulating light generation modules;
   configuring the program adjustable optical parameter control module to generate stimulating light with different parameters at regular intervals, control a light generation module of a corresponding wavelength to generate a stimulating light signal with a corresponding parameter, and output the stimulating light signal through the optical fiber coupler;
   forming a seal between the measuring electrode and a cell membrane of the cell to be detected;
   treating the cell by measuring the cell membrane current change under different photostimulation conditions using a glass tube microelectrode, wherein the cell is cultured isolatedly or has been separated prior to treatment;
   performing scanning measurement of photostimulation parameters using the photostimulation device in a multi-parameter progressive regulation mode, wherein the multi-parameter progressive regulation-mode includes scanning measurements that start below a light energy threshold and continue until either a light energy threshold is established or the cell is found to be not optically regulated;
   measuring specificity by performing membrane current measurement through progressive regulation of other optical parameters with different wavelengths of stimulating light, respectively, to detect wavelength specificity generated by a cell membrane current stimulated by the light; and
   determining a cell membrane current change as representation of presence or absence of cell activity.

2. The isolated cell membrane potential detection method of claim 1, wherein the measuring electrode is a glass tube microelectrode including a glass tube and a measuring electrode, wherein the glass tube has a conical shape with an open tip; and the measuring electrode is inserted into the glass tube from a tail part of the glass tube, while the glass tube is filled with an electrode internal solution.

3. The isolated cell membrane potential detection method of claim 1, wherein the measuring electrode includes a tip and the tip has a diameter smaller than a cell body.

4. The isolated cell membrane potential detection method of claim 1, wherein the system further comprises a reference electrode immersed in the cell bath and connected to a signal ground terminal of the signal acquisition amplifier.

5. The isolated cell membrane potential detection method of claim 1, wherein the cell to be detected is a single isolated cell, which is a cell that is isolatedly cultured or has been surgically dissected.

* * * * *